(12) United States Patent
Nomura

(10) Patent No.: US 12,029,918 B2
(45) Date of Patent: Jul. 9, 2024

(54) DOSE MANAGEMENT DEVICE AND RECORDING MEDIUM

(71) Applicant: Konica Minolta, Inc., Tokyo (JP)

(72) Inventor: Seiji Nomura, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 560 days.

(21) Appl. No.: 17/314,722

(22) Filed: May 7, 2021

(65) Prior Publication Data

US 2021/0370093 A1 Dec. 2, 2021

(30) Foreign Application Priority Data

May 27, 2020 (JP) ................................. 2020-091875

(51) Int. Cl.
| | |
|---|---|
| *A61N 5/10* | (2006.01) |
| *G16H 20/40* | (2018.01) |
| *G16H 30/20* | (2018.01) |
| *G16H 30/40* | (2018.01) |

(52) U.S. Cl.
CPC ........... *A61N 5/1031* (2013.01); *G16H 20/40* (2018.01); *G16H 30/20* (2018.01); *G16H 30/40* (2018.01); *A61N 2005/1059* (2013.01)

(58) Field of Classification Search
CPC ......... A61N 2005/1059; A61N 5/1031; G16H 20/40; G16H 30/20; G16H 30/40
See application file for complete search history.

(56) References Cited

U.S. PATENT DOCUMENTS

| | | | | |
|---|---|---|---|---|
| 8,412,544 B2 * | 4/2013 | Reiner | .................... | G16H 30/40 600/300 |
| 2008/0103834 A1 * | 5/2008 | Reiner | .................... | G16H 20/40 705/3 |
| 2012/0022845 A1 * | 1/2012 | Bismuth | ................ | A61B 6/542 703/11 |
| 2012/0106817 A1 * | 5/2012 | Shih | ........................ | A61B 6/583 382/131 |
| 2013/0274537 A1 * | 10/2013 | Park | ....................... | G16H 20/40 600/1 |

(Continued)

FOREIGN PATENT DOCUMENTS

| | | |
|---|---|---|
| JP | 2007-181482 A | 7/2007 |
| JP | 2013-192697 A | 9/2013 |

(Continued)

OTHER PUBLICATIONS

Notice of Reasons for Refusal issued in corresponding Japanese Application No. 2020-091875 mailed Jul. 25, 2023 (9 pages).

*Primary Examiner* — Mark R Gaworecki
(74) *Attorney, Agent, or Firm* — Osha Bergman Watanabe & Burton LLP

(57) ABSTRACT

A dose management device manages dose information of radiation doses in radiation events where radiographic images are generated in response to radiation on a subject. The dose management device includes a controller that acquires a target piece of the dose information, identifies a radiographic image corresponding to the target piece based on correspondence between each of the radiographic images and a piece of the dose information in a radiation event in which the radiographic images are generated, and outputs the identified radiographic image.

10 Claims, 8 Drawing Sheets

(56) References Cited

U.S. PATENT DOCUMENTS

| | | | | |
|---|---|---|---|---|
| 2015/0196267 A1* | 7/2015 | Ohishi | ............... | A61B 6/584 |
| | | | | 378/20 |
| 2019/0066827 A1* | 2/2019 | Noro | ............... | G16H 15/00 |
| 2019/0070435 A1* | 3/2019 | Joe Anto | ............ | A61N 5/103 |
| 2019/0083047 A1* | 3/2019 | Miller | ............... | A61B 6/542 |
| 2019/0240508 A1* | 8/2019 | Friman | ............ | G06F 3/0346 |
| 2020/0069277 A1* | 3/2020 | Dorn | ............... | G16H 30/20 |
| 2020/0100755 A1* | 4/2020 | Dorn | ............... | A61B 6/544 |

FOREIGN PATENT DOCUMENTS

| | | | |
|---|---|---|---|
| JP | 2016-013250 A | | 1/2016 |
| JP | 2017-213288 A | | 12/2017 |
| JP | 2017213288 A | * | 12/2017 |
| JP | 2018-000739 A | | 1/2018 |

* cited by examiner

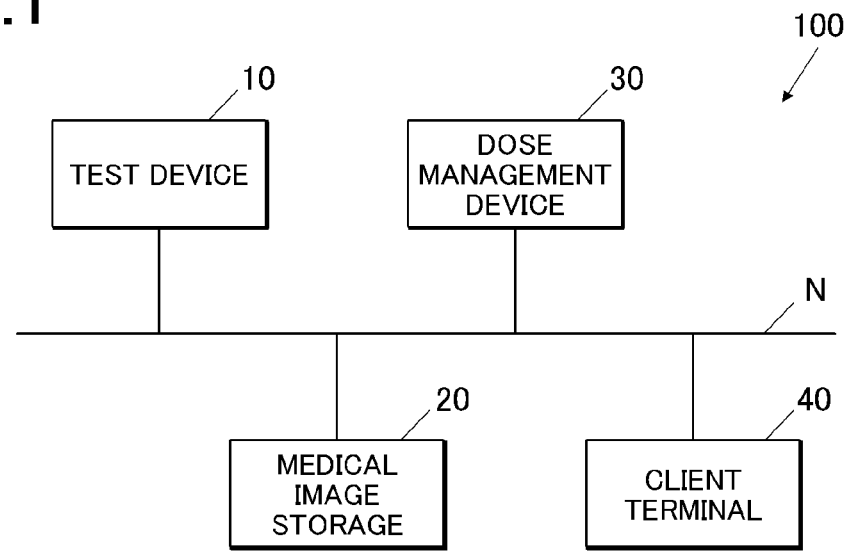
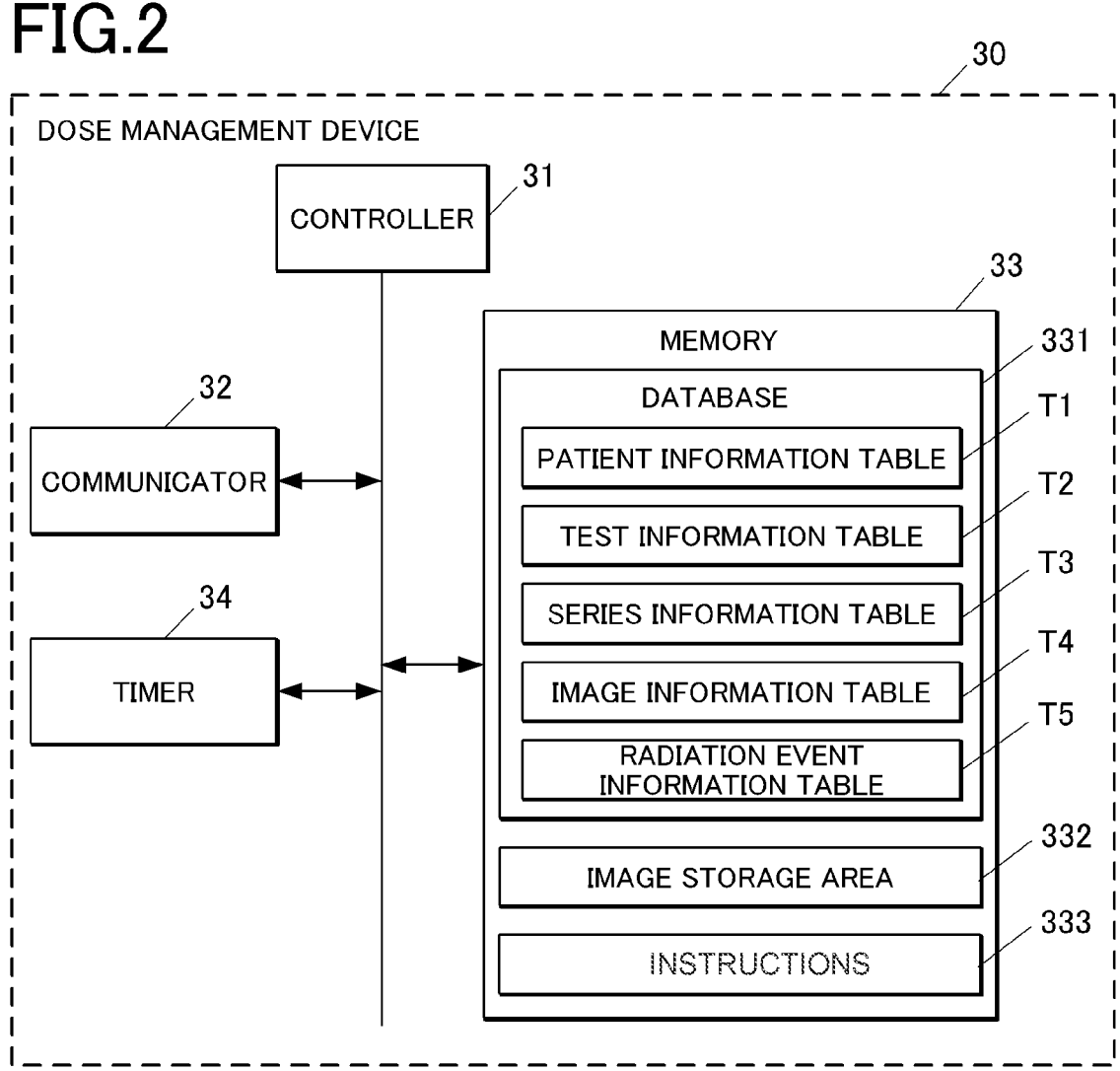

FIG. 9

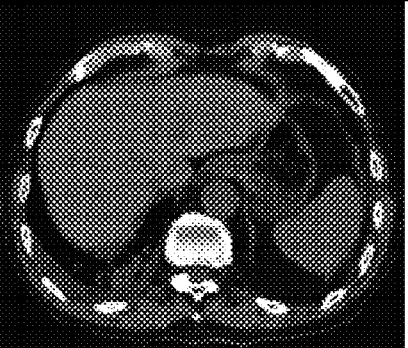

| PATIENT INFORMATION | | | | | |
|---|---|---|---|---|---|
| PATIENT NAME | PATIENT ID | AGE | SEX | HEIGHT | WEIGHT |
| Konica Hanako | 12317012 | 73 | FEMALE | 145.5cm | 50.0kg |

| TEST INFORMATION | | | | | |
|---|---|---|---|---|---|
| TEST TIME AND DATE | | ... | ... | ... | ... |
| 2019/05/25 22:29:20 | | ... | ... | ... | ... |

| RADIATION EVENT LIST | | | | | | |
|---|---|---|---|---|---|---|
| CTDIvol | DLP | VOLTAGE | CURRENT | MAXIMUM CURRENT | RADIATION TIME | SCAN LENGTH |
| 0.14 | 10.79 | 120 | 35 | 35 | 7830 | 770 |
| 5.31 | 311.60 | 120 | 227 | 259 | 5000 | 830 |
| 7.27 | 671.88 | 120 | 555 | 739 | 2870 | 928 |

| RADIATION DETAILS | |
|---|---|
| RADIATION TIME | 5000ms |
| VOLTAGE | 120kV |
| CURRENT | 227mA |
| DLP | 311.60mGy.cm |
| CTDIvol | 5.31mGy |
| SCAN LENGTH | 830mm |
| PHANTOM | IEC Body Dosimetry Phantom |
| ROTATIONAL SPEED | ... |
| PITCH | ... |

IMAGE

DOSE MANAGEMENT DEVICE AND RECORDING MEDIUM

CROSS-REFERENCE TO RELATED APPLICATIONS

The entire disclosure of Japanese patent application No. 2020-091875, filed on May 27, 2020, is incorporated herein by reference.

BACKGROUND

Technical Field

The present invention relates to a dose management device and a recording medium.

Description of Related Art

In the field of medical care, a test device (modality) such as a CT (Computed Tomography) device that irradiates a patient with radiation to generate a radiographic image as a medical image is used. In a test using such a test device, in order to appropriately manage a radiation exposure dose, a dose of radiation used in the test is confirmed, and shooting conditions such as a radiation dose in the test device are adjusted. For example, according to JP 2013-192697A, a graph shows relation between radiation doses under various shooting conditions and granularity representing image quality of acquired radiographic images. A shooting condition which improves image quality and which limits the radiation dose within a predetermined range is specified.

However, it is usually difficult to determine whether the radiation dose is appropriate based solely on a value of a radiation dose. It is necessary to confirm a patient's body shape, etc. based on a radiographic image generated in response to radiation, and to determine whether it is an appropriate radiation dose for the patient. In order to manage the exposure dose, it is necessary to look for and display a radiographic image corresponding to a radiation dose to be paid attention each time, in addition to displaying information on the radiation dose. It brings a complicated operation.

SUMMARY

One or more embodiments provide a dose management device and a recording medium that easily determine whether a radiation dose is appropriate.

According to one or more embodiments, a dose management device that manages dose information of radiation doses in radiation events where radiographic images are generated in response to radiation on a subject includes:
  an acquisition unit that acquires a target piece of the dose information which is selected from pieces of the dose information in a predetermined selection method; and
  an output controller which (i) identifies a radiographic image corresponding to the target piece of the dose information, which is acquired by the acquisition unit, based on correspondence between each radiographic image and a piece of the dose information in a radiation event in which the radiographic image is generated among the radiation events, and which (ii) outputs the identified radiographic image.

According to one or more embodiments, a non-transitory recording medium stores computer readable instructions for a computer of a dose management device that manages dose information of radiation doses in radiation events in which radiographic images are generated in response to radiation on a subject, the instructions causing the computer to function as:
  an acquisition unit that acquires a target piece of the dose information which is selected from pieces of the dose information in a predetermined selection method; and
  an output controller which (i) identifies a radiographic image corresponding to the target piece of the dose information, which is acquired by the acquisition unit, based on correspondence between each radiographic image and a piece of the dose information in a radiation event in which the radiographic image is generated among the radiation events, and which (ii) outputs the identified radiographic image.

BRIEF DESCRIPTION OF DRAWINGS

The advantages and features provided by one or more embodiments of the present invention will become more fully understood from the detailed description given hereinbelow and the appended drawings which are given by way of illustration only, and thus are not intended as a definition of the limits of the present invention.

FIG. 1 shows a system configuration example of a medical information management system.

FIG. 2 is a block diagram showing functional configuration of a dose management device.

FIG. 9 shows an example of a dose information display screen.

DETAILED DESCRIPTION

Figure 3:
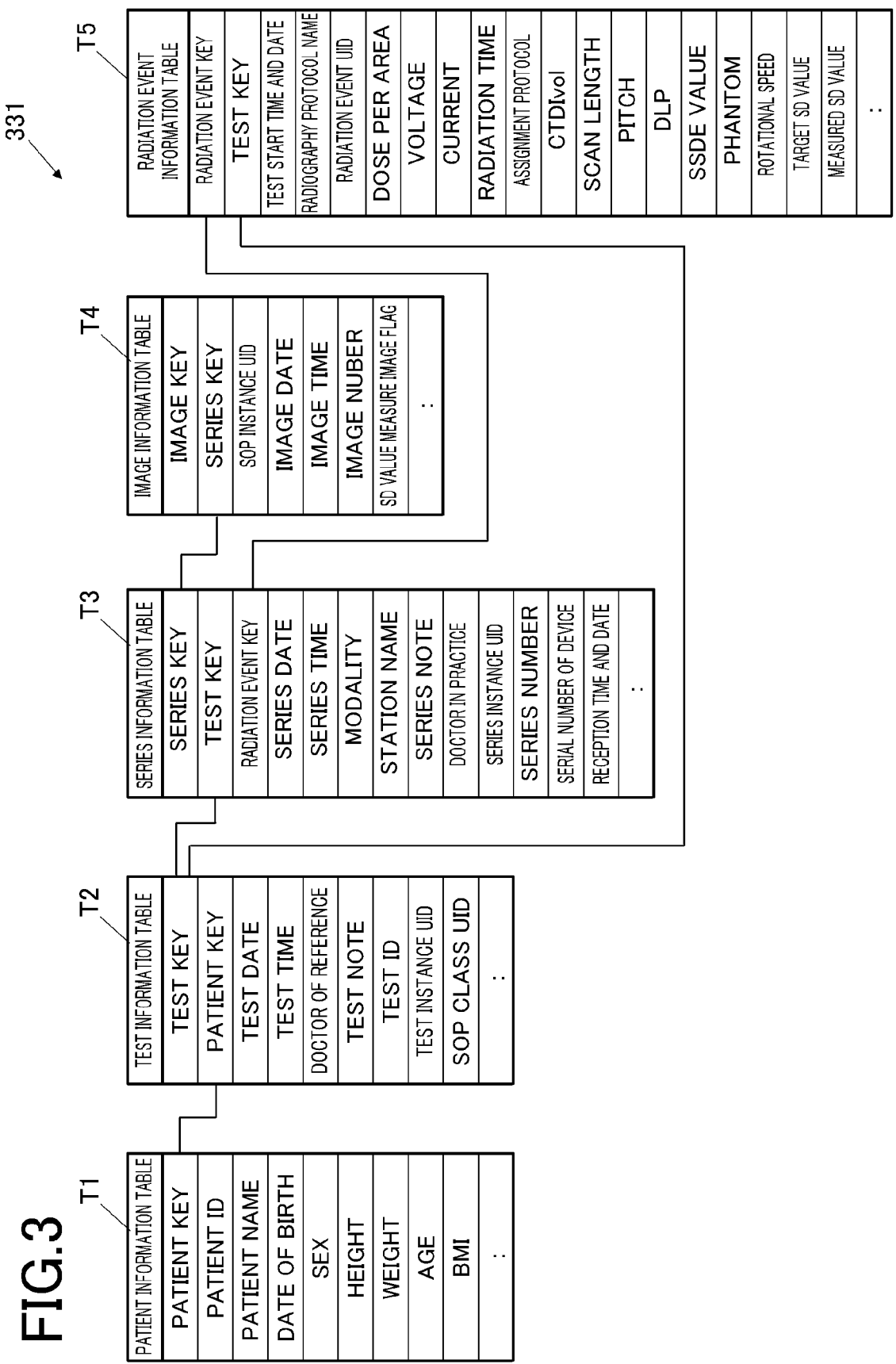
FIG. 3 shows data configuration in a database.

Hereinafter, embodiments of a dose management device and a recording medium will be described. However, the present invention is not limited to the illustrated examples.

FIG. 1 shows a system configuration example of a medical information management system 100.

As shown in FIG. 1, the medical information management system 100 includes a test device 10, a medical image storage 20, a dose management device 30, a client terminal 40, and the like. The devices are connected so as to be able to transmit and receive data via a communication network N such as a LAN (Local Area Network) and a WAN (Wide Area Network). The devices that constitute the medical information management system 100 conform to HL7 (Health Level Seven) and DICOM (Digital Image and Communications in Medicine) standards. Communication between the devices is carried out in accordance with HL7 and DICOM. The medical information management system 100 may include multiple test devices 10 and/or multiple client terminals 40.

The test device 10 is a modality such as a CT device or an X-ray imaging device (DR, CR). The test device 10 operates in response to operation of a manipulator on a console (not shown). The test device 10 exposes a patient (subject) to radiation, and generates image data of a radiographic image (for example, CT image) as a medical image based on detection result of radiation. In accordance with the DICOM standard, the test device 10 attaches supplementary information to the radiographic image by writing the supplementary information in a header of an image file of the medical image, and generates a DICOM image file. The supplementary information includes patient information, test information, series information, and image information.

The patient information is information about a patient. The patient information includes patient ID, patient name, date of birth, sex, height, weight, age, and BMI. The patient ID is identification information for identifying a patient.

The test information is information about a test. The test information includes test ID, test date, test time, test note, and test instance UID. The test instance UID is identification information for identifying a test, and uniqueness is guaranteed in the DICOM standard.

Series information is information about series. The series information includes series instance UID, series number, series date, series time, modality (CT, DR, CR, etc.), and series note. The series instance UID is identification information for identifying series, and uniqueness is guaranteed in the DICOM standard.

The image information is information about an image. The image information includes SOP instance UID, image date, image time, and image number. The SOP instance UID is identification information for identifying a radiographic image, and uniqueness is guaranteed in the DICOM standard. The image number is a number in shooting order of tomography (CT image) generated in one scan.

The test device 10 generates an RDSR (Radiation Dose Structured Report) including dose information of a test performed in the test device 10. The test device 10 transmits image data and the RDSR of a generated radiographic image to the medical image storage 20 and the dose management device 30.

The RDSR is information in accordance with the DICOM standard, and is one of data formats of data that includes radiation dose information. The dose information is information of a radiation dose (amount of energy) of radiation on a patient in a radiation test. The dose information includes indicators representing a radiation dose, such as a DLP (Dose Length Product) and a CTDIvol. The dose information may also include information of amounts that correlate with a radiation dose, such as voltage applied for radiation, current, and radiation time. The test device 10 generates an RDSR for each radiation event.

The radiation event is a series of radiation operations for a subject (usually a series of radiation operations under one radiation condition). In each radiation event, one or more radiographic images are generated in response to radiation. In a case where radiation condition is changed, or in a case where an imaging target site of a subject and its state (administration of a contrast agent, etc.) are changed, a radiation event occurs every time radiation is newly started. Specifically, one or more radiographic images are generated in one radiation event. The radiographic images are associated with one series. The series is newly set in, for example, a case where a viewpoint of taken image is switched, such as a case where a cross-sectional setting of CT is changed or a case where a magnification setting of an image is changed. A plurality of radiographic images may be associated with one series. For example, in a CT device, a tomography taken continuously in one radiation event is associated with one series. Radiographic images associated with one series is also described as "series of images" below.

The medical image storage 20 stores and manages image data of radiographic images generated in the test device 10 and dose information included in an RDSR for each patient and for each test. The medical image storage 20 is, for example, a PACS (Picture Archiving and Communication System).

The dose management device 30 is a computer device that manages dose information at the time of taking radiographic images.

FIG. 2 is a block diagram showing functional configuration of the dose management device 30.

As shown in FIG. 2, the dose management device 30 includes a controller 31 (computer), a communicator 32, memory 33, and a timer 34. Those parts are connected by bus.

The controller 31 includes a CPU (Central Processing Unit), ROM (Read Only Memory), and RAM (Random Access Memory), and comprehensively controls processing operation of the parts of the dose management device 30. Specifically, the CPU reads instructions 333 stored in the memory 33 and develops it in the RAM. The CPU performs processing of various kinds according to the instructions 333. The CPU performs the instructions 333 so that the controller 31 functions as an acquisition unit, an output controller, a first memory controller, and a second memory controller.

The communicator 32 is constituted by a network interface or the like. The communicator 32 transmits and receives data to/from external devices connected via the communication network N. For example, the communicator 32 receives, from the test device 10, image data and an RDSR of a radiographic image acquired by radiographing a patient. The communicator 32 may receive the image data and the RDSR of a radiographic image from the medical image storage 20.

The memory 33 is constituted by an HDD (Hard Disk Drive), nonvolatile semiconductor memory, etc., and stores various data. For example, the memory 33 has a database 331 and an image storage area 332. The instructions 333 are stored in the memory 33. The instructions 333 may be stored in the ROM of the controller 31.

Supplementary information (header information) of a file of radiographic images stored in the image storage area 332 and radiation event information (dose information, etc.) of tests are stored in the database 331 in a searchable manner.

FIG. 3 shows data configuration in the database 331. The database 331 includes a patient information table T1, a test information table T2, a series information table T3, an image information table T4, and a radiation event information table T5.

Information about a patient is stored in the patient information table T1. Information in the patient information table T1 is mainly information acquired from an RDSR, but is supplemented from supplementary information of a DICOM image as necessary. In the patient information table T1, a patient key, which is the primary key, is associated with patient ID, patient name, date of birth, sex, height, weight, age, BMI, etc.

Information about a test is stored in the test information table T2. Information in the test information table T2 is mainly information acquired from an RDSR, but is supplemented from supplementary information of a DICOM image as necessary. In the test information table T2, a test key, which is the primary key, is associated with patient key (patient to be tested), test date, test time, doctor of reference, test note, test ID, test instance UID, SOP class UID, etc.

Information about a series in supplementary information of a DICOM image is stored in the series information table T3. In the series information table T3, a series key, which is the primary key, is associated with test key (test to which a series belongs), radiation event key (radiation event to which the series belongs), series date, series time, modality, station name, series note, doctor in practice, series instance UID, series number, serial number of device, reception time and date, etc. Of them, the radiation event key is given based on result of matching processing. In the matching processing, correspondence between a series (series of images) and a radiation event (i.e. RDSR) is determined. The reception time and date is the time and date when image data of radiographic images belonging to the series is received.

Information about image in supplementary information of a DICOM image (radiographic image) is stored in the image information table T4. In the image information table T4, an image key, which is the primary key, is associated with series key (series to which an image belongs), SOP instance UID, image date, image time, image number, SD value measure image flag, etc.

The image information table T4 is associated with the series information table T3 via the series key. The series information table T3 is associated with the radiation event information table T5 via the radiation event key. According to the database 331, correspondence between the image information tables T4 and the radiation event information tables T5, in other words, correspondence between radiographic images and RDSRs (therefore, dose information) is acquired. The database 331 corresponds to "dose correspondence information" which identifies correspondence between a radiographic image and dose information in a radiation event in which the radiographic image is generated among radiation events.

Information (radiation event information) for each radiation generated in a test is stored in the radiation event information table T5. In the radiation event information table T5, the radiation event key, which is the main key, is associated with test key (test to which a radiation event belongs), test start time and date, radiography protocol name, radiation event UID, dose per area, voltage, current, radiation time, assignment protocol, CTDIvol, scan length, pitch, DLP, SSDE value, phantom, rotational speed, target SD value, measured SD value, etc. The radiation event UID is identification information for identifying a radiation event, and uniqueness is guaranteed in the DICOM standard. The target SD value is an SD value (SD value included in the DICOM information) set in a test, and indicates target image quality (granularity, etc.). The measured SD value is an SD value measured from a radiographic image acquired by a test, and indicates actual image quality (granularity, etc.) of a radiographic image.

Image data of radiographic images and the like are stored in the image storage area 332.

Figure 4:
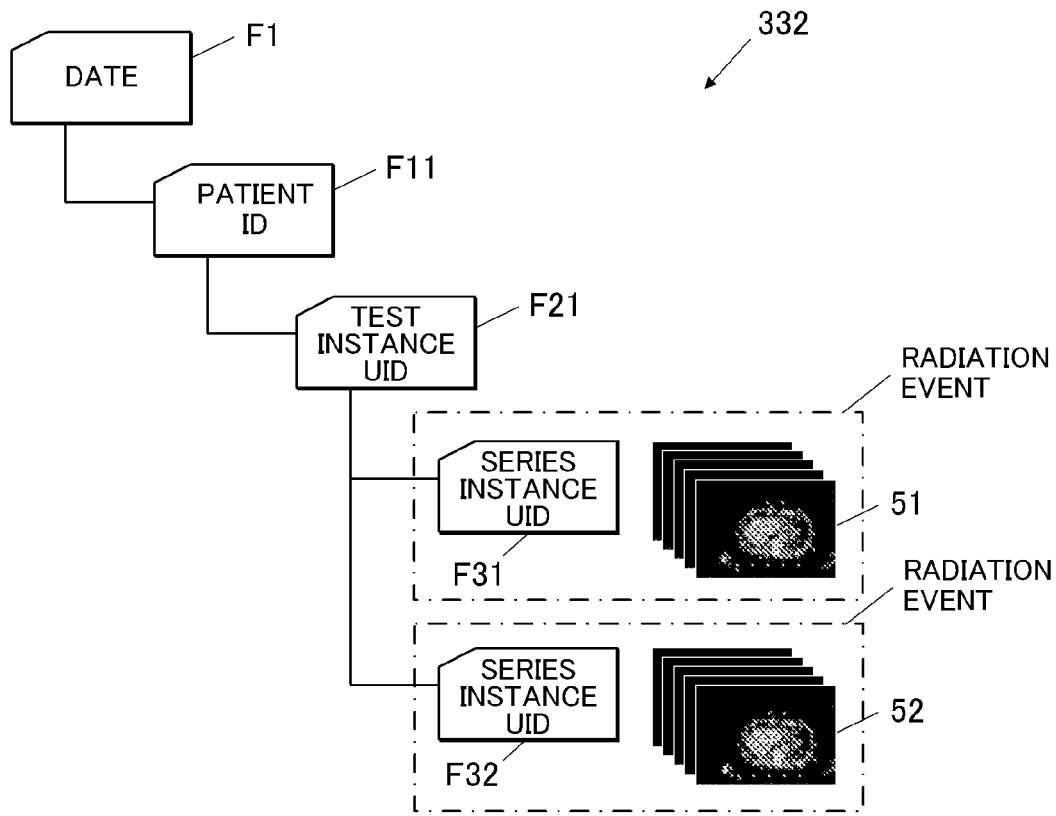
FIG. 4 shows folder configuration in an image storage area.

FIG. 4 shows folder configuration in the image storage area 332. Each data is stored in folders tiered in order of date, patient ID, test instance UID, and series instance UID.

Specifically, a "Date" folder F1 is made for each date when the dose management device 30 receives (acquires) radiographic images.

In a lower hierarchy of the "Date" folder F1, a "Patient ID" folder F11 is made for each patient.

In a lower hierarchy of the "Patient ID" folder F11, a "Test Instance UID" folder F21 is made for each test.

In a lower hierarchy of the "Test Instance UID" folder F21, "Series Instance UID" folders F31, F32 are made for each series.

Image data of radiographic images 51, 52 belonging to the corresponding series are stored in the "Series Instance UID" folders F31, F32, respectively. A file name of the image data of each of the radiographic images 51, 52 is "SOP instance UID" of the radiographic images. In FIG. 4, radiographic images (series of images) stored in one "Series Instance UID" folder F31 (or F32) correspond to one radiation event. That is, the radiographic images 51, 52 are acquired in a state where the images are grouped according to radiation events, and are stored. The present invention is not limited to this.

Two or more series of images may correspond to one radiation event.

In the image storage area 332, a separate folder is made for each date, each patient, each test, and each series. This provides fast access to files. A folder where a target radiographic image is stored, and a file of the radiographic image are identified from the DICOM information without access to the database 331.

The timer 34 shown in FIG. 2 has a timer circuit (RTC: Real Time Clock). The timer circuit clocks present time and date and outputs it to the controller 31.

Next, the client terminal 40 will be described. The client terminal 40 is a computer device such as a computer used by a doctor. A doctor views radiographic images, dose information, and the like of a test at the client terminal 40.

Figure 5:
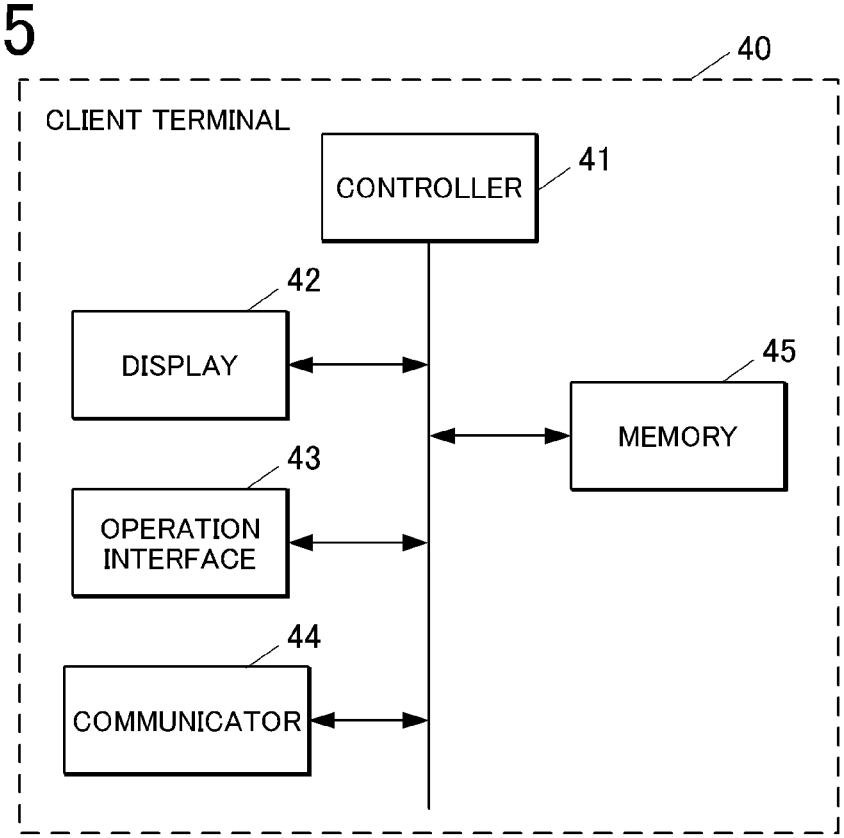
FIG. 5 is a block diagram showing functional configuration of a client terminal.

FIG. 5 is a block diagram showing functional configuration of the client terminal 40.

As shown in FIG. 5, the client terminal 40 includes a controller 41, a display 42, an operation interface 43, a communicator 44, and memory 45. Those parts are connected by bus.

The controller 41 is constituted by a CPU, ROM, RAM, and the like, and comprehensively controls processing operation of the parts of the client terminal 40. Specifically, the CPU reads various processing instructions stored in the ROM and develops them in the RAM. The CPU cooperates with the instructions to perform processing of various kinds.

The display 42 includes a monitor such as an LCD (Liquid Crystal Display), and displays various screens according to instructions of display signals input by the controller 41.

The operation interface 43 includes a keyboard equipped with cursor keys, letter/number input keys, various function keys, etc. and a pointing device such as a mouse. The operation interface 43 outputs operation signals input by key operation on the keyboard and mouse operation to the controller 41. The operation interface 43 may have a touch panel piled on the monitor of the display 42.

The communicator 44 is constituted by a network interface or the like, and transmits and receives data to/from external devices connected via the communication network N.

The memory 45 is constituted by a HDD, nonvolatile semiconductor memory, or the like, and stores various data.

Next, operation of devices in the medical information management system 100 will be described.

In the medical information management system 100, the test device 10 generates a radiation event and generates radiographic images. Image data of the radiographic images and an RDSR of the radiation event are transmitted to the medical image storage 20 and the dose management device 30.

The dose management device 30 performs data registration processing in which the received image data of radiographic images and the RDSR are registered in the database 331.

Figure 6:
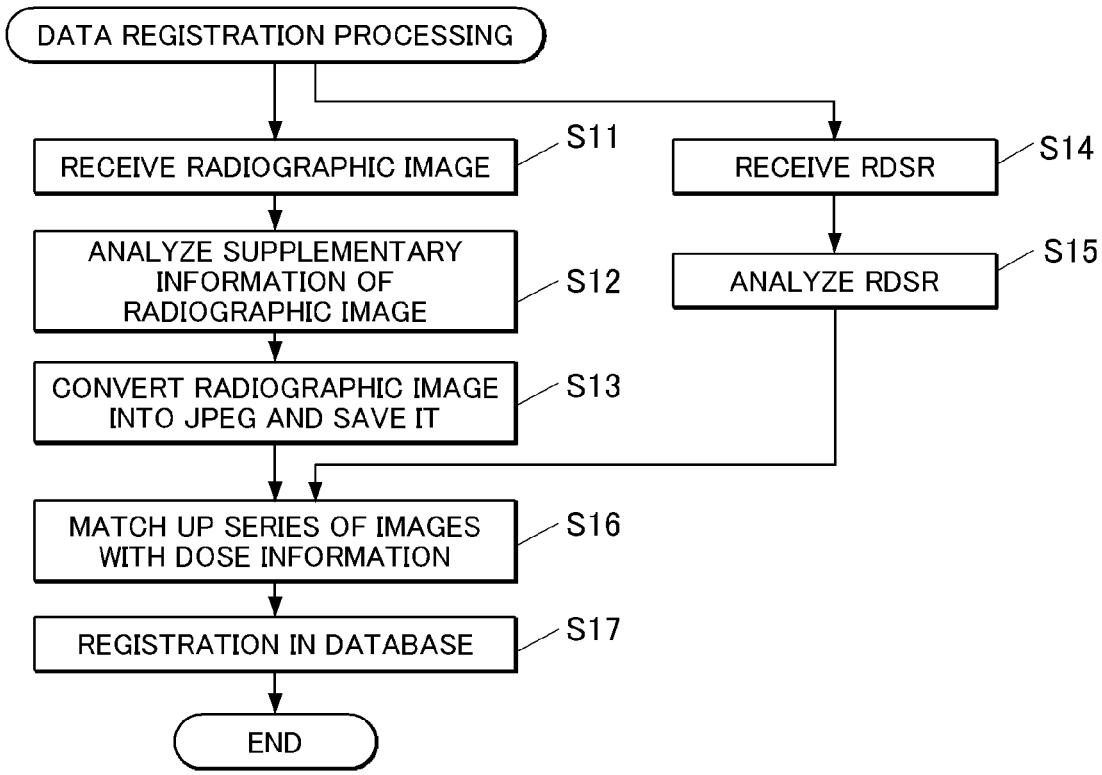
FIG. 6 is a flowchart showing control procedure in data registration processing.

FIG. 6 is a flowchart showing control procedure in the data registration processing by the controller 31.

In the test device 10, an X-ray CT test or the like is performed on a subject. The test device 10 transmits image data of radiographic images such as CT images (tomography) and an RDSR to the dose management device 30.

The controller 31 of the dose management device 30 receives the image data of radiographic images (Step S11) and also receives the RDSR (Step S14) via the communicator 32.

The controller 31 analyzes supplementary information for each of the received radiographic images (Step S12). Specifically, the controller 31 acquires items in patient information, test information, series information, and image information from the supplementary information of the radiographic image.

Next, the controller 31 (second memory controller) reduces an amount of image data of each of the received radiographic images, and saves it in the image storage area 332 of the memory 33 (Step S13). For example, the controller 31 converts the image data of the radiographic image from bitmap data to JPEG data, and saves them.

Specifically, in Step S13, in a case where a part or all of the "Date" folder, "Patient ID" folder, and "Test Instance UID" folder corresponding to contents of the supplementary information of the received radiographic image does not exist, the controller 31 generates those folders. The controller 31 makes a "Series Instance UID" folder corresponding to a series instance UID included in series information of the received radiographic image in the lower hierarchy of the "Test Instance UID" folder. The controller 31 groups the image data of radiographic images converted to JPEG data according to series, and stores them as a series of images in the "Series Instance UID" folder.

The controller 31 (second memory controller) sets a save period of image data of radiographic images for each radiation event. Deletion processing at a time when the save period passes will be described later.

On the other hand, when the controller 31 receives the RDSR from the test device 10 in Step S14, the controller 31 analyzes the received RDSR (Step S15). Specifically, the controller 31 acquires items of patient information (patient ID, etc.), test information (test instance UID, etc.), dose information, and the like from the RDSR one by one.

The controller 31 (first memory control means) matches the series of images saved in Step S13 with the dose information of the RDSR analyzed in Step S15 (Step S16). The controller 31 registers the result of matching, the supplementary information of the radiographic image, and information acquired by analyzing the RDSR in the database 331 of the memory 33 (Step S17).

The matching in Step S16 is processing of identifying a radiation event in which a series of images is generated and matching the series of images with the radiation event. The method of matching is not particularly limited. For example, a radiation event UID to be associated with an RDSR is included in supplementary information of a radiographic image, and the RDSR is associated based on the radiation event UID. Alternatively, a time zone of a radiation event is compared with a generation time of a radiographic image.

In Step S17, the controller 31 records the radiation event key of the radiation event corresponding to the series identified by matching in the series information table T3.

Thereby, in the database 331, a series and radiographic images belonging to the series are associated with dose information of a radiation event.

In other words, in Steps S16 and S17, the controller 31 (first memory controller) associates dose information of a received RDSR with radiographic images generated in a radiation event corresponding to the dose information, and generates (usually updates) the database 331 as dose correspondence information. The controller 31 stores it in the memory 33. In one or more embodiments, the processing of generating dose correspondence information includes processing of updating the database 331 by adding new data to the database 331 as dose correspondence information.

In Step S17, contents of the patient information table T1, the test information table T2, the series information table T3, the image information table T4, and the radiation event information table T5 are updated based on information acquired by analyzing supplementary information of radiographic images and an RDSR.

After the processing of Step S17, the controller 31 terminates the data registration processing.

In the above data registration processing, a case where the dose management device 30 receives radiographic images and an RDSR from the test device 10 is described. However, the dose management device 30 may receive the radiographic images and the RDSR from the medical image storage 20. The dose management device 30 may not simultaneously receive the radiographic images and the RDSR from the test device 10 or the medical image storage 20.

Next, operation in dose management of the medical information management system 100 will be described.

In the medical information management system 100, various information related to radiation dose information of a radiation event is displayed on the display 42 in response to operation on the operation interface 43 of the client terminal 40. Specifically, a scatter plot screen 421 (see FIG. 8) showing radiation dose information of each of radiation events is displayed on the display 42. By selecting one of points on the scatter plot on the scatter plot screen 421, a dose information display screen 422 (information display screen) (see FIG. 9) including detailed information of a radiation event corresponding to the selected point is displayed on the display 42.

A control method in data use processing including display processing of the scatter plot screen 421 and the dose information display screen 422 will be described.

Figure 7:
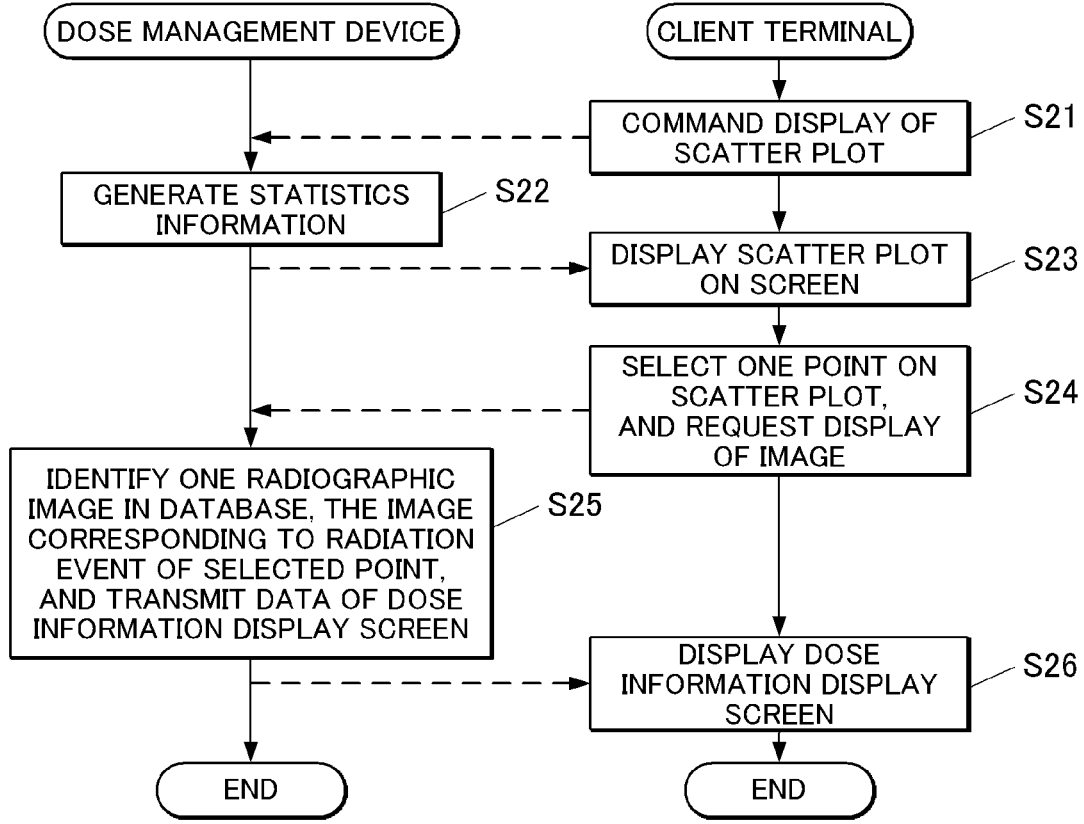
FIG. 7 is a ladder chart showing control procedure in data use processing.

FIG. 7 is a ladder chart showing control procedure in the data use processing performed by the dose management device 30 and the client terminal 40.

When the data use processing is started, first, the controller 41 of the client terminal 40 transmits contents of instructions to the dose management device 30 in response to input operation (Step S21). In the input operation, search conditions (patient, test, modality, weight, etc.) are specified, and display of the scatter plot is commanded.

The dose management device 30 receives the display command of the scatter plot. The controller 31 of the dose management device 30 refers to the database 331 of the memory 33, and generates statistical information for displaying the scatter plot that meets the search conditions (Step S22). In one or more embodiments, the statistical information includes a pair of DLP data as dose information of each radiation event and data of a patient's weight in the radiation event. Specifically, the controller 31 acquires a "weight" for each patient included in the patient information table T1. The controller 31 identifies a test in the test information table T2 which is associated with the patient (patient key). The controller 31 identifies radiation event information in the radiation event information table T5 which is associated with the specified test (test key). The controller 31 acquires a "DLP" included in the identified radiation event information. In a case where multiple pieces of radiation event information are associated with a test for one patient, there are multiple "DLPs" of the patient. There are pairs of a patient's weight and a DLP, the number of the pairs being the same as the number of DLPs.

The controller 31 (output controller) generates data of the scatter plot screen 421 including an image of a scatter plot based on the generated statistical information. The scatter plot has a horizontal axis of weight and a vertical axis of DLP. The controller 31 displays the scatter plot screen 421 on the display 42 of the client terminal 40 based on the data. That is, the controller 31 (output controller) transmits the data to display points on the coordinate plane on the display 42. One axis of coordinates indicates an amount of radiation dose. The points correspond to pieces of dose information. Specifically, the controller 31 makes the communicator 32 transmit data of the scatter plot screen 421 to the client terminal 40. After the controller 41 of the client terminal 40 receives the data, the controller 41 displays the scatter plot screen 421 on the display 42 based on the received data (Step S23).

Figure 8:
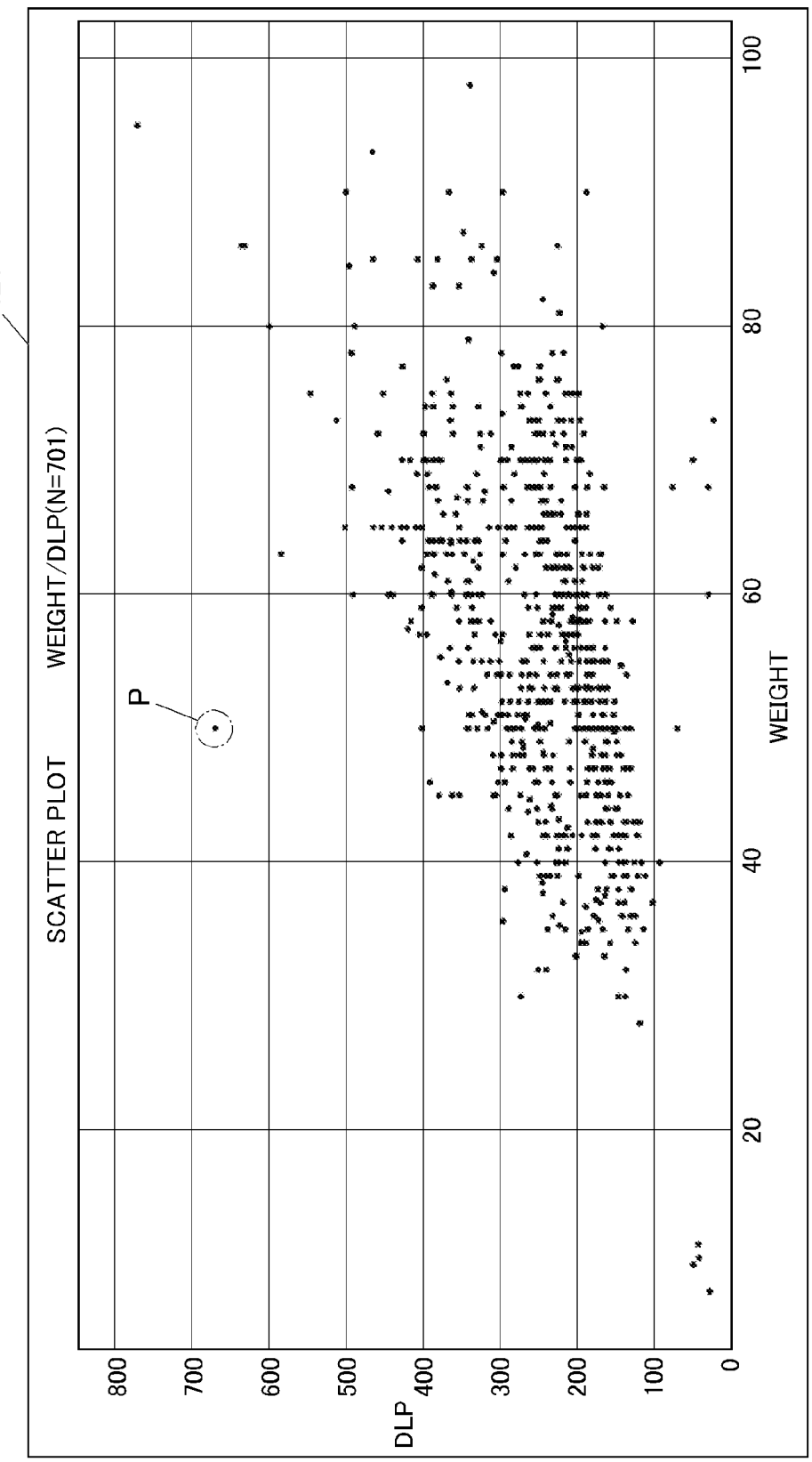
FIG. 8 shows an example of a scatter plot screen.

FIG. 8 shows an example of a scatter plot screen 421 displayed on the display 42 of the client terminal 40. On the scatter plot screen 421, DLP values for weights are plotted. Each of points distributed on the scatter plot corresponds to one radiation event information (radiation event UID). Therefore, one radiation event (i.e., dose information) is selected in a method of selecting one of the points.

Input operation of selecting one of the points on the scatter plot is performed on the operation interface 43 of the client terminal 40. The controller 41 transmits a request for displaying the dose information display screen 422 to the dose management device 30 (Step S24). The dose information display screen 422 concerns a radiation event corresponding to the selected one point. In this example, an abnormal value (for example, point P in FIG. 8) on the scatter plot screen 421 of FIG. 8 is selected. The abnormal value is a point that is far from other points among the points displayed on the scatter plot, and is also called an outlier. Especially in a radiation event corresponding to the abnormal value, there is a high need to confirm that ultraviolet rays are radiated at an appropriate radiation dose. For this confirmation, it is necessary to display the dose information display screen 422 and refer to detailed information including a radiographic image.

The controller 31 of the dose management device 30 receives the request for displaying the dose information display screen 422. In Step S25, the controller 31 of the dose management device 30 acquires data on a radiation event corresponding to the selected point (in this example, the abnormal value) from the database 331 and the image storage area 332 of the memory 33. Thus, the controller 31 (acquisition unit) acquires dose information corresponding to a selected radiation event in a method of selecting one of points on the scatter plot. Specifically, the controller 31 identifies a radiation event and dose information corresponding to a selected point. The controller 31 acquires various data of a test to which the radiation event belongs. The controller 31 acquires image data of one radiographic image associated with the radiation event (dose information). The controller 31 generates data of the dose information display screen 422 based on those acquired information. The controller 31 displays a dose information display screen 422 on the display 42 of the client terminal 40 based on the data. Specifically, the controller 31 makes the communicator 32 transmit the data of the dose information display screen 422 to the client terminal 40. The client terminal 40 receives the data. The controller 41 of the client terminal 40 displays the dose information display screen 422 on the display 42 based on the received data.

FIG. 9 shows an example of a dose information display screen 422 displayed on the display 42 of the client terminal 40. The dose information display screen 422 includes a patient information area 61, a test information area 62, a radiation event list area 63, a radiation details area 64, and a radiographic image region 65.

Information about a patient tested in a selected radiation event is displayed in the patient information area 61.

Information about a test to which the selected radiation event belongs is displayed in the test information area 62.

A list of radiation events associated with the test is displayed in the radiation event list area 63. That is, not only the radiation event selected on the scatter plot but all the radiation events in the test to which the selected radiation event belongs are listed in the radiation event list area 63. In the radiation event list area 63, one radiation event selected on the scatter plot is clearly indicated by highlighting. In the example shown in FIG. 9, a list of three radiation events in the test is displayed. The second radiation event from the top is clearly indicated as one radiation event selected on the scatter plot.

Dose information of the radiation event highlighted in the radiation event list area 63 is displayed in the radiation details area 64. In the example shown in FIG. 9, radiation time, voltage, current, DLP, CTDIvol, scan length, phantom, rotational speed and pitch correspond to the dose information, though the present invention is not limited to this example.

Any item on the database 331 can be set as an item displayed in the patient information area 61, the test information area 62, the radiation event list area 63, or the radiation details area 64.

Of radiographic images (series of images) generated in the radiation event corresponding to the point selected on the scatter plot, one radiographic image is displayed as a representative image in the radiographic image region 65. The representative image is, for example, a radiographic image in the middle of order in which the radiographic images are taken. This is because, in a series of images, radiographic images are often taken before and after a radiographic image actually used for reading. A radiographic image suitable for a representative image is often around the middle of shooting order.

The present invention is not limited to this. In a case where two or more radiographic images are generated in a radiation event, any radiographic image selected in a predetermined method out of the two or more radiographic images may be displayed. For example, the first radiographic image in a series of images may be displayed as the representative image.

Thus, the controller 31 (output controller) identifies a radiographic image generated in a radiation event corresponding to one point selected on the scatter plot. The controller 31 displays the identified radiographic image on the display 42 of the client terminal 40.

The controller 31 (output controller) displays the dose information display screen 422 including the radiation event list area 63 on the display 42. In the radiation event list area 63, the radiation event in which the identified radiographic image is generated is clearly indicated. The controller 31 displays the identified radiographic image in the dose information display screen 422.

Based on the radiographic image displayed in the radiographic image region 65, a patient's build and the like are confirmed. Result of the confirmation of the radiographic image and dose information in the radiation details area 64 are considered together. Thereby, it is confirmed whether the patient's exposure dose at the selected radiation event is appropriate.

In the dose information display screen 422, the radiation event corresponding to one point selected on the scatter plot is clearly indicated by highlighting in the radiation event list area 63 in advance. One radiographic image generated by the radiation event is automatically selected and is displayed in the radiographic image area 65. Therefore, it is easily determined whether an exposure dose at the selected radiation event is appropriate.

In the dose information display screen 422, when input operation of selecting one radiation event in the radiation event list area 63 is performed, display contents are switched to information of the selected radiation event. That is, the selected radiation event is highlighted, and dose information of the radiation event is displayed in the radiation details area 64. One radiographic image generated in the radiation event is displayed in the radiographic image region 65. Thus, information of any radiation event included in a test can be confirmed on the dose information display screen 422.

After processing of steps S25 and S26, the controllers 31, 41 terminate the data use processing.

The above data use processing is an example in which a scatter plot representing correlation between weight and DLP is displayed. The present invention is not limited to this. For example, as an index of a patient's build, BMI or the like may be used instead of weight. Various indices other than DLP may be used as dose information.

Next, data deletion processing performed by the dose management device 30 will be described.

In the dose management device 30, image data of radiographic images are acquired one by one for dose management. The image data is stored in the memory 33 one by one. In order to prevent lack of space in the memory 33, a period for storing image data of radiographic images is set. The data deletion processing is performed for image data when the save period for the image data passes.

Figure 10:
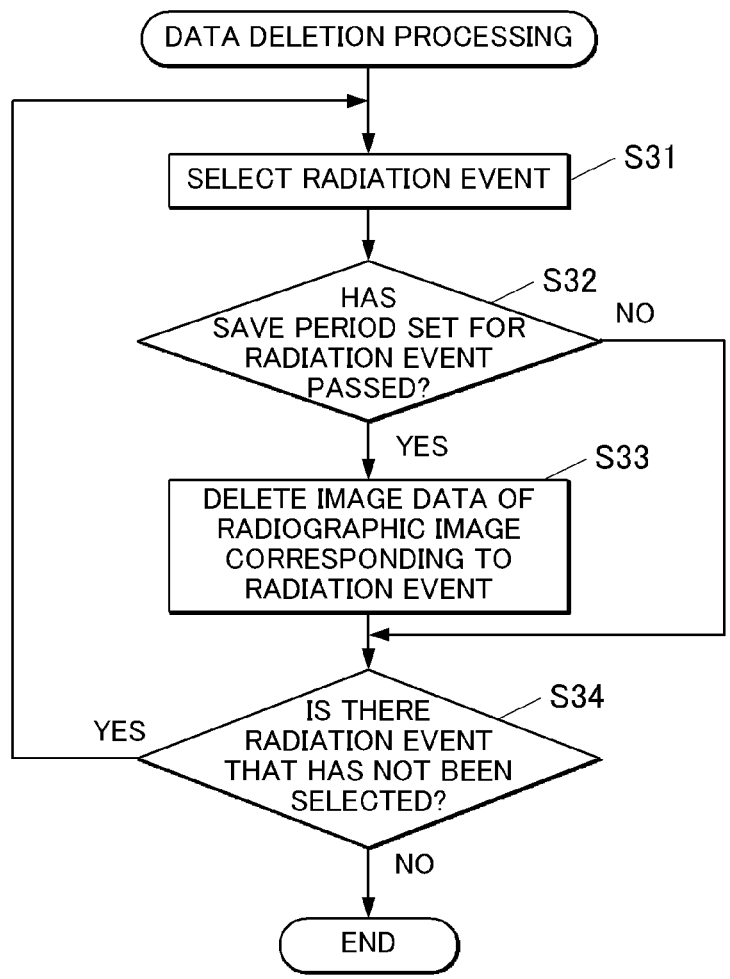
FIG. 10 is a flowchart showing control procedure in data deletion processing by a controller.

FIG. 10 is a flowchart showing control procedure in the data deletion processing by the controller 31.

The data deletion processing is performed periodically, such as once a week and once a month.

When the data deletion processing is started, the controller 31 (second memory controller) selects one radiation event referring to the database 331 (Step S31). The controller 31 determines whether the save period set for the selected radiation event has passed (Step S32). Specifically, the controller 31 acquires the "reception time and date" of the series belonging to the selected radiation event from the series information table T3. The controller 31 acquires present time and date from the timer 34. The controller 31 compares a period between the reception time and the present time with the save period. Thereby, the controller 31 determines whether the save period has passed.

In a case where the controller 31 determines that the save period has passed ("YES" in Step S32), the controller 31 (second memory controller) deletes image data of radiographic images associated with the radiation event from the memory 33 (Step S33).

In a case where Step S33 is terminated, or in a case where the controller 31 determines that the save period has not passed in Step S32 ("NO" in Step S32), the controller 31 determines whether there is a radiation event that has not been selected yet (Step S34). In a case where the controller 31 determines that there is a radiation event that has not been selected yet ("YES" in Step S34), the controller 31 returns processing to Step S31. In a case where the controller 31 determines that all the radiation events have been selected ("NO" in Step S34), the controller 31 terminates the data deletion processing.

In the above, the save period was set for each radiation event. The present invention is not limited to this. For example, the save period may be set for each series.

Modification

Next, a modification of the above embodiments will be described.

In one or more embodiments, the radiation event key is included in the series information table T3 as shown in FIG. 3. As a result, a series (and radiographic images belonging to the series) is associated with a radiation event, and the radiographic images are associated with the radiation event via the series. However, the present invention is not limited to this.

Figure 11:
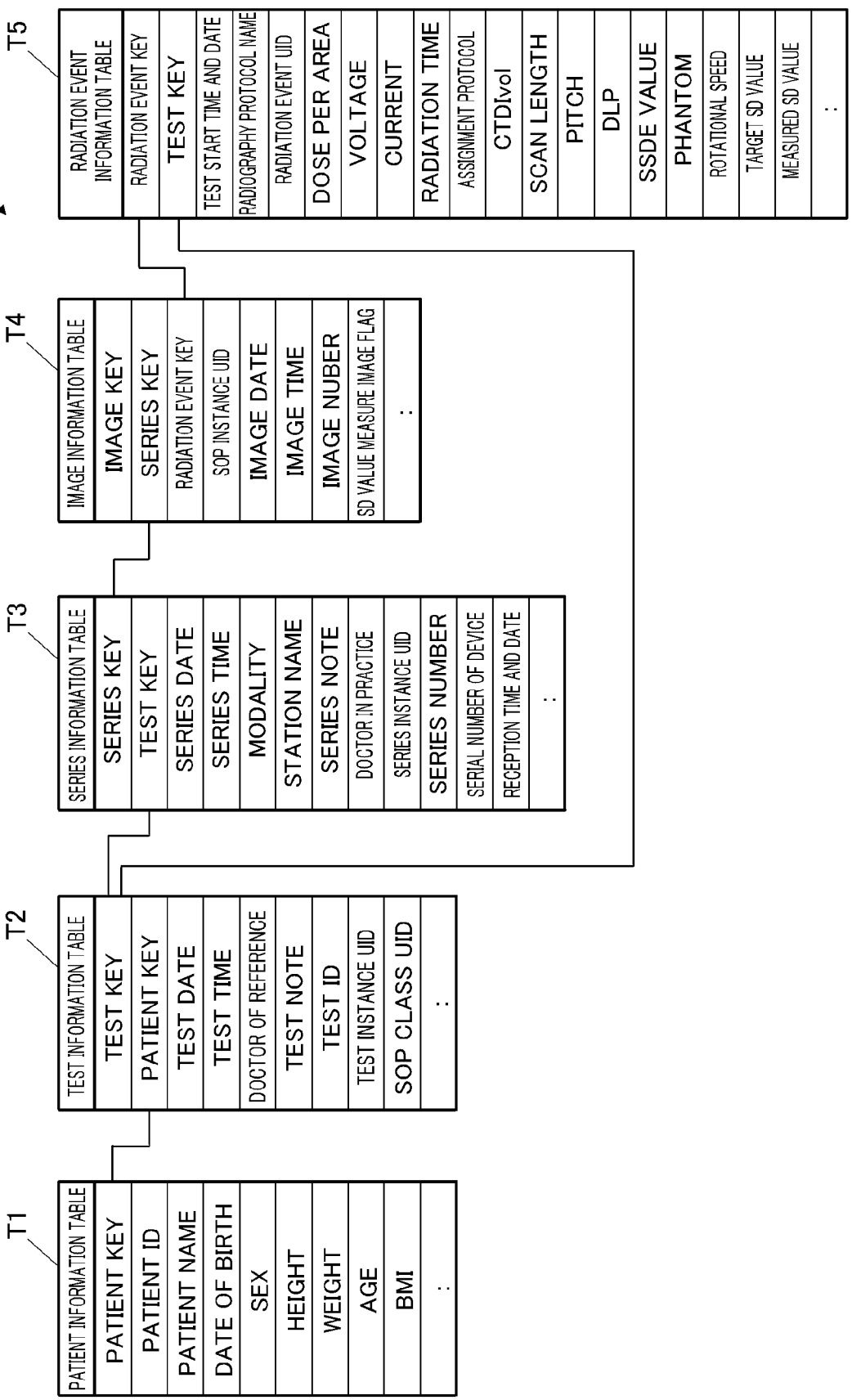
FIG. 11 shows another example of the data configuration in the database.

For example, as shown in FIG. 11, radiographic images may be directly associated with a radiation event by including the radiation event key in the image information table T4. To manage such a database 331, a radiation event UID to be associated with an RDSR is included in supplementary information of radiographic images.

The method of associating radiographic images with a radiation event is not limited to that. For example, table data that associates a radiation event with a series or radiographic images may be provided separately from the database 331.

As described above, the dose management device 30 according to one or more embodiments manages dose information of radiation doses in radiation events. In a radiation event, one or more radiographic images are generated according to radiation on a subject. The dose management device 30 includes the controller 31. The controller 31 (acquisition unit) acquires dose information selected in a predetermined selection method. Based on the database 331, the controller 31 (output controller) identifies radiographic images corresponding to the acquired dose information and outputs the identified radiographic images. Correspondence between radiographic images and dose information in a radiation event in which the radiographic images are generated among radiation events is specified in the database 331.

Thereby, radiographic images generated in a radiation event is directly displayed and confirmed by simple operation of selecting dose information of the radiation event. Even if multiple radiation events are included in one test, it is not necessary to look for and display radiographic images of a desired radiation event among a large number of radiographic images of the multiple radiation events. Radiographic images corresponding to dose information is easily confirmed. Whether a radiation dose is appropriate is easily determined while a build of a patient known from radiographic images is considered.

The controller 31 (output controller) displays identified radiographic images on the display 42 of the client terminal 40. Therefore, radiographic images are visually and easily confirmed on a screen of the display 42.

The controller 31 (output controller) displays the dose information display screen 422 that clearly indicates a radiation event in which specified radiographic images are generated on the display 42. Therefore, even if multiple radiation events are included in one test, a radiation event corresponding to selected dose information is easily identified on the dose information display screen 422.

The controller 31 (output controller) displays an identified radiographic image on the dose information display screen 422. Therefore, a radiation event corresponding to selected dose information and radiographic images generated in the radiation event are easily confirmed on one screen. Thus, dose information, etc. of a radiation event and build of a patient known from radiographic images are confirmed on one screen. Whether an exposure dose in a selected radiation event is appropriate is easily determined.

The controller 31 (acquisition unit) acquires dose information selected in the method of selecting one of pieces of dose information displayed in a predetermined way on the display 42. Since candidates of dose information to be selected is presented in advance, desired dose information is easily selected.

The controller 31 (output controller) displays points corresponding to pieces of dose information on a coordinate plane on the display. One axis of coordinates indicates an amount of radiation dose. The controller 31 (acquisition unit) acquires dose information selected in the method of selecting one of the points. Thus, desired dose information is selected in a method in which dose information is easily recognized by eyes.

In a case where two or more radiographic images are generated in a radiation event corresponding to acquired dose information, the controller 31 (output controller) outputs one radiographic image selected in a predetermined method out of the two or more radiographic images. Since a radiographic image representing a radiation event is automatically selected and displayed, a user does not need to look for an appropriate one from radiographic images. Therefore, it is easier to determine whether an exposure dose is appropriate.

The dose management device includes the memory 33. The controller 31 (first memory controller) generates the database 331 and stores it in the memory 33. In the database 331, received dose information is associated with radiographic images generated at a radiation event corresponding to the dose information. The controller 31 identifies the radiographic images corresponding to the dose information based on the database 331. Since the database 331 is updated according to occurrence of a radiation event, whether an exposure dose is appropriate is determined for any radiation event including the latest radiation event.

The controller 31 acquires image data of radiographic images. The controller 31 (second memory controller) groups image data according to radiation events and stores them in the memory 33. Thus, radiographic images in each radiation event are appropriately managed by simple processing.

The controller 31 (second memory controller) reduces an amount of image data of radiographic images and stores it in the memory 33. Therefore, memory space of the memory 33 is effectively used. The memory 33 can store image data of more radiographic images.

The controller 31 acquires the save period of image data of radiographic images set for a radiation event. The controller 31 (second memory controller) deletes the image data of the radiation event from the memory 33 after the save period passes. It prevents failure that memory space of the memory 33 is insufficient and that the latest image data cannot be stored.

The instructions 333 according to one or more embodiments make the controller 31, which is a computer provided in the dose management device 30, function as:
an acquisition unit that acquires dose information selected in a predetermined method; and
an output controller which identifies radiographic images corresponding to dose information acquired by the acquisition unit based on the database 331 and which outputs the identified radiographic images.

In the database 331, correspondence between the radiographic images and the dose information of the radiation event in which the radiographic images are generated among radiation events is identified. With such instructions 333, radiographic images generated in a radiation event are directly displayed and confirmed through simple operation of selecting dose information of the radiation event. Even in a case where one test includes multiple radiation events, it is not necessary to look for and display radiographic images of a desired radiation event among a large number of radiographic images of the multiple radiation events. Since radiographic images corresponding to a dose information is easily confirmed, whether a radiation dose is appropriate is easily determined while a build of a patient known from the radiographic images is considered.

The above embodiments are examples of a dose management device. The present invention is not limited to this. Detailed configuration and detailed operation of part of the device can be changed within the scope of the present invention.

For example, the above embodiments are examples in which multiple radiographic images are generated for one radiation event in a test by a CT device or the like. The present invention is not limited to this. For example, one or more embodiments of the present invention can be applied also to a case where one radiographic image is generated for one radiation event in X-ray plain radiography or the like. Dose information in this case is managed for each radiation for generating a single radiographic image. Therefore, each piece of dose information corresponds to one radiographic image.

In a case where the dose management device 30 is provided with an operation interface and a display, and a user can directly operate the dose management device 30, the dose management device 30 may accept user operation. In that case, the contents displayed on the display 42 of the client terminal 40 in the above embodiments are displayed on the display of the dose management device 30.

The client terminal 40 may have functions of the dose management device 30. The client terminal 40 has all of the functions shared by the dose management device 30 and the client terminal 40 in the above embodiments. In that case, the client terminal 40 is the dose management device.

The client terminal 40 may be a console used for controlling the test device 10.

The above embodiments are examples in which the memory 33 of the dose management device 30 is provided with the database 331 and the image storage area 332. The present invention is not limited to this. For example, a database server or the like outside the dose management device 30 may be provided with the database 331. Data is acquired from the database server when it is necessary. Similarly, an external storage of the dose management device 30 may store image data of radiographic images. Data is acquired from the storage when it is necessary.

The above embodiments are examples in which a radiation event and dose information are selected in the method of selecting one of points on a scatter plot. The present invention is not limited to this. Dose information can be selected in any method that can identify desired one among pieces of dose information.

Although displaying on the display 42 is shown as an example of output of radiographic images, the present invention is not limited to this. The output of radiographic images may be, for example, print on paper.

In the above description, the memory 33 and the ROM is used as examples of a computer-readable medium storing instructions for executing processing of various kinds. The present invention is not limited to that example. A nonvolatile memory, such as flash memory, and a portable storage medium, such as CD-ROM, can also be used as a computer-readable storage medium. A carrier wave may be applied as a medium that provides data of instructions through a communication line.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A dose management device that manages dose information of radiation doses in radiation events where radiographic images are generated in response to radiation on a subject, the dose management device comprising:
   a controller that:
      acquires a target piece of the dose information,
      identifies a radiographic image corresponding to the target piece based on correspondence between each of the radiographic images and a piece of the dose information in a radiation event in which the radiographic images are generated,
      displays the identified radiographic image on a display, and
      displays points corresponding to the dose information on a coordinate plane that includes a coordinate axis indicating the radiation doses.

2. The dose management device according to claim 1, wherein the controller further displays an information display screen that indicates the radiation event in which the identified radiographic image is generated.

3. The dose management device according to claim 2, wherein the controller further displays the identified radiographic image on the information display screen.

4. The dose management device according to claim 1, wherein the controller further displays a piece of the dose information on the display.

5. The dose management device described in claim 1, further comprising:
   a memory, wherein
   the controller generates dose correspondence information and stores the dose correspondence information in the memory,
   in the dose correspondence information, each received piece of the dose information is associated with a radiographic image generated at a radiation event corresponding to the received piece of the dose information, and
   the controller further identifies the radiographic image corresponding to the target piece of the dose information based on the dose correspondence information.

6. The dose management device according to claim 1, further comprising:
   a memory, wherein
   the controller acquires image data of the radiographic images, groups the image data according to the radiation events, and stores the image data in the memory.

7. The dose management device according to claim 6, wherein the controller reduces an amount of the image data before storing the image data in the memory.

8. The dose management device according to claim 6, wherein
   the controller acquires a save period of the image data set for the radiation events, and
   when the save period set for one of the radiation events passes, the controller deletes the image data corresponding to the one of the radiation events.

9. A dose management device that manages dose information of radiation doses in radiation events where radiographic images are generated in response to radiation on a subject, the dose management device comprising:
   a controller that:
      acquires a target piece of the dose information,
      identifies a radiographic image corresponding to the target piece based on correspondence between each of the radiographic images and a piece of the dose information in a radiation event in which the radiographic images are generated, and
      outputs the identified radiographic image, wherein
   in a case where two or more of the radiographic images are generated in the radiation event corresponding to the target piece, the controller outputs one of the two or more radiographic images.

10. A non-transitory recording medium storing computer readable instructions for a computer of a dose management device that manages dose information of radiation doses in radiation events in which radiographic images are generated in response to radiation on a subject, the instructions causing the computer to:
   acquire a target piece of the dose information;
   identify a radiographic image corresponding to the target piece based on correspondence between each of the radiographic images and a piece of the dose information in a radiation event in which the radiographic image is generated,
   display the identified radiographic image on a display, and
   display points corresponding to the dose information on a coordinate plane that includes a coordinate axis indicating the radiation doses.

* * * * *